US00PP29937P2

(12) United States Plant Patent
Klinger, Jr.

(10) Patent No.: US PP29,937 P2
(45) Date of Patent: Dec. 4, 2018

(54) ***VIBURNUM* PLANT NAMED 'COMPACT01'**

(50) Latin Name: *Viburnum odoratissimum*
Varietal Denomination: COMPACT01

(71) Applicant: Paul Klinger, Jr., Bushnell, FL (US)

(72) Inventor: Paul Klinger, Jr., Bushnell, FL (US)

(73) Assignee: Plant Development Services Inc., Loxley, AL (US)

( * ) Notice: Subject to any disclaimer, the term of this patent is extended or adjusted under 35 U.S.C. 154(b) by 78 days.

(21) Appl. No.: 15/731,183

(22) Filed: Apr. 28, 2017

(51) Int. Cl.
*A01H 5/00* (2018.01)
*A01H 5/02* (2018.01)

(52) U.S. Cl.
USPC ..... Plt./226
CPC ..... *A01H 5/02* (2013.01)

(58) Field of Classification Search
USPC ..... Plt./226
CPC ..... A01H 5/02
See application file for complete search history.

*Primary Examiner* — Kent L Bell
(74) *Attorney, Agent, or Firm* — Cassandra Bright

(57) ABSTRACT

A new and distinct *Viburnum* cultivar named 'COMPACT01' is disclosed, characterized by a small foliage, typically around ⅓ the size of the typical *Viburnum odoratissimum*. Plants are distinctively short and compact, having an internode length on average about ½ the size of typical *Viburnum odoratissimum*. Growth is controlled and compact, reducing maintenance within the landscape. The new variety is a *Viburnum odoratissimum*, normally produced as an outdoor garden or container plant.

2 Drawing Sheets

Figure 1:
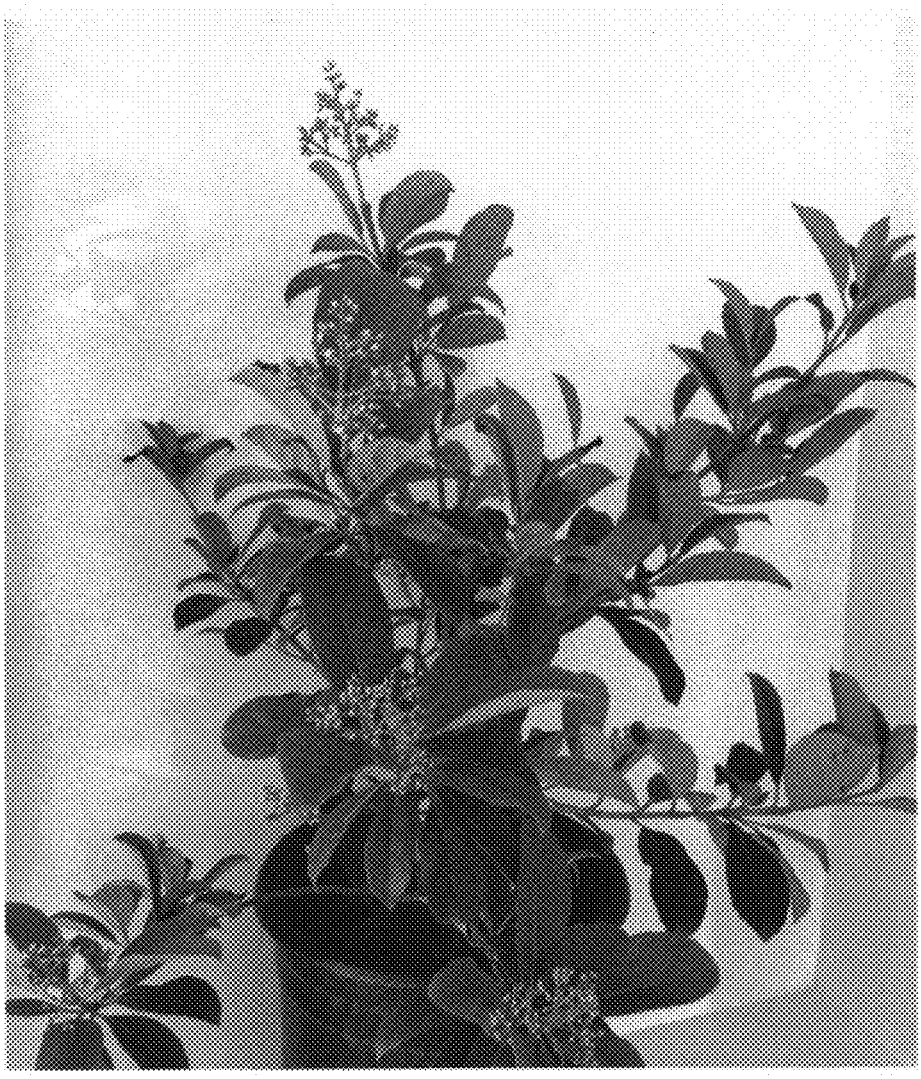

Latin name of the genus and species: *Viburnum odoratissimum.*

Variety denomination: 'COMPACT01'.

BACKGROUND OF THE INVENTION

The new *Viburnum* cultivar originated as a chance seedling discovered in a commercial planting of an unnamed, unpatented *Viburnum odoratissimum* plant widely sold in the commercial horticulture trade. A single seedling with small foliage and compact plant morphology was discovered by the inventor in a commercial planting of an unnamed, unpatented *Viburnum odoratissimum* plant. The inventor selected this interesting seedling at a commercial nursery in Center Hill, Fla. in 2010.

Asexual reproduction of the new cultivar 'COMPACT01' by softwood cuttings was first performed during the Spring of 2011, at a commercial nursery in Center Hill, Fla. Subsequent asexual propagation has shown that the unique features of this cultivar are stable and reproduced true to type in 2 successive generations.

SUMMARY OF THE INVENTION

The cultivar 'COMPACT01' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'COMPACT01' These characteristics in combination distinguish 'COMPACT01' as a new and distinct *Viburnum* cultivar:

1. Foliage approximately ⅓ the size of the typical *Viburnum odoratissimum.*
2. Short plant height.

3. Compact growth.
4. More densely branching than typical *Viburnum odoratissimum.*
5. Internode length approximately ½ the length of typical *Viburnum odoratissimum.*
6. Controlled and compact growth reduces maintenance within the landscape.

PARENT COMPARISON

The pollen and seed parent are assumed to be the same unpatented, unnamed *Viburnum odoratissimum* plant commonly sold in the trade. Plants of the new cultivar, 'COMPACT01' are similar to plants of the assumed parent in most horticultural characteristics. Plants of the new cultivar 'COMPACT01', however, differ in the following;

1. Foliage of the new variety is approximately ⅓ the size of foliage of the assumed parent.
2. Plant habit of the new variety is much more compact.
3. Internode length of the new variety is approximately ½ the length of the assumed parent plant.
4. Plants of the new variety are shorter than those of the assumed parent.

COMMERCIAL COMPARISON

Plants of the new cultivar 'COMPACT01' can be compared to the unpatented commercial variety *Viburnum* 'Emerald Jewel'. These varieties are similar in most horticultural characteristics, however 'COMPACT01' differs in the following:

1. The new variety has much smaller foliage, approximately ½ to ⅓ the size of this comparator.
2. Plant habit of the new variety is much more compact.
3. Internode length of the new variety is approximately ½ the length of this comparator 4. Plants of the new variety are shorter than those of 'Emerald Jewel'.

Plants of the new cultivar 'COMPACT01' can be compared to the unpatented commercial variety *Viburnum* 'Emerald Lustre'. These varieties are similar in most horticultural characteristics, however 'COMPACT01' differs in the following:

1. The new variety has much smaller foliage, approximately ½ to ⅓ the size of this comparator.
2. Plant habit of the new variety is much more compact and dense.
3. Internode length of the new variety is approximately ½ or less than the internode length of this comparator
4. Plants of the new variety are shorter than those of 'Emerald Lustre', this comparator forms a large shrub or small tree, the new variety forms a mid-sized shrub.
5. Foliage of 'Emerald Lustre' can be slightly copper colored in Spring, a characteristic not observed in the new variety.

BRIEF DESCRIPTION OF THE PHOTOGRAPHS

The accompanying photograph in FIG. 1 illustrates in full color a typical plant of 'COMPACT01' grown outdoors in a 2 gallon nursery pot, in Loxley, Ala.

Figure 2:
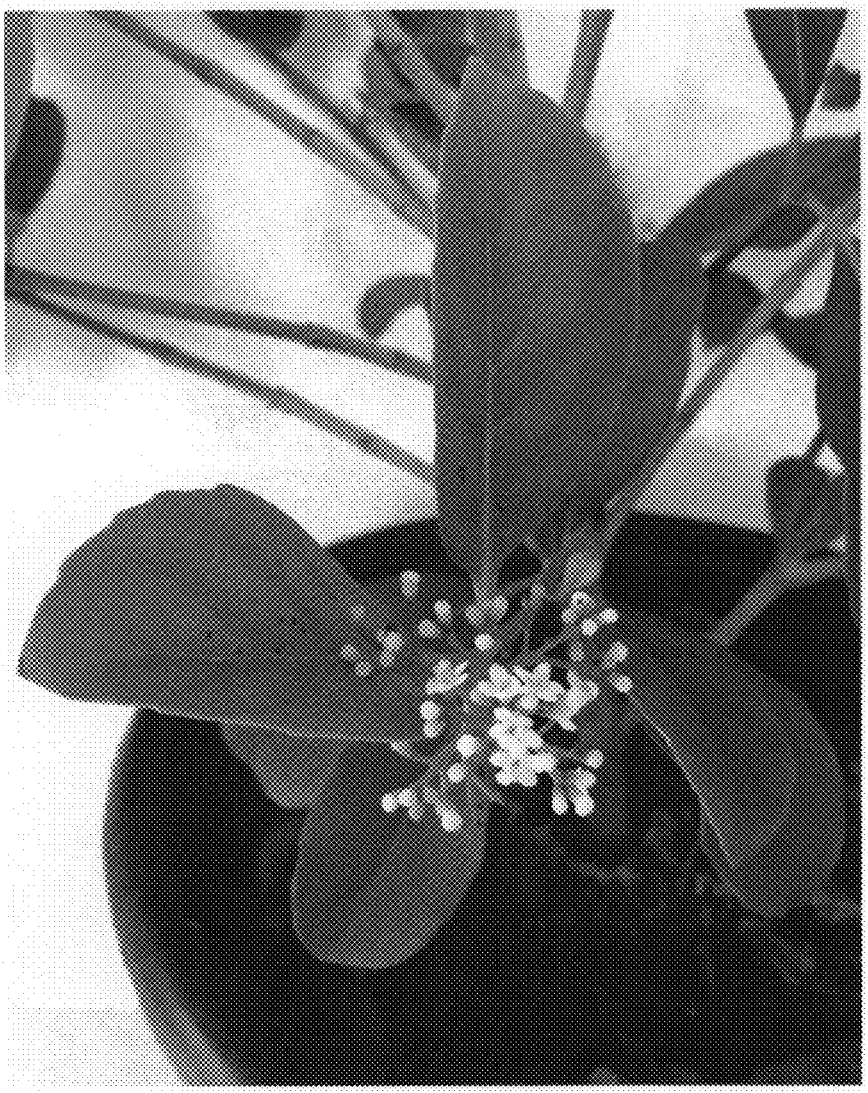

FIG. 2 illustrates in full color a typical inflorescence of 'COMPACT01'. Age of the plant photographed is approximately 2 years.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'COMPACT01' plants grown in a commercial nursery in Loxley, Ala. Measurements were taken during Spring of 2017. The plants were 2-3 years old in 2 gallon containers. The growing temperature ranged from approximately 2° C. to 27° C. Measurements and numerical values represent averages of typical plant types.

Botanical classification: *Viburnum odoratissimum* 'COMPACT01'.

PROPAGATION

Time to initiate roots: About 30 days at approximately 24° C.

Root description: Dense density freely branching. Root thickness from thick to thin. White to brown in color, not effectively measured with a color chart.

Time to produce a rooted young plant: About 120 days at 24° C.

PLANT

Plant type: Perennial shrub.

Age of plant described: Approximately 3 years old.

Growth habit: Evergreen shrub.

Pot size of plant described: 3 gallon pot.

Overall plant shape: Outward "V" shape.

Height: 60 cm.

Plant spread: 70 cm.

Growth rate: Moderate.

Plant vigor: Good.

Branching characteristics: Opposite, basal branching. Pinching required.

Length of primary lateral branches: 20 to 35 cm.

Diameter of lateral branches: 1 cm.

Quantity of lateral branches: About 5 to 7 lateral branches per main branch.

Stem:

*Stem appearance*.—Round.

*Stem strength*.—Strong.

*Stem color*.—New growth near RHS Green 143C. Older growth near Greyed-Green 197D.

*Pubescence*.—New growth glabrous, older growth slightly scaly.

*Aspect*.—Upright about 35° to 45° from center of plant.

Internode length: Average 3 to 7 cm.

FOLIAGE

Leaf:

*Arrangement*.—Opposite.

*Leaf shape*.—Obovate.

*Average length*.—Average range 4 to 7 cm, including petiole.

*Average width*.—3.0 cm.

*Apex*.—Acute.

*Base*.—Attenuate.

*Margin*.—Infrequent broad dentations, more frequent towards apex.

*Texture of top surface*.—Glabrous.

*Texture of bottom surface*.—Glabrous.

*Appearance of top surface*.—Moderately glossy.

*Appearance of bottom surface*.—Matte with shiny veins.

*Color*.—Young foliage upper side: Near Yellow-Green 144A. Young foliage under side: Near Green 138B. Mature foliage upper side: Near RHS Green 137B. Mature foliage under side: Near RHS Green 138A.

*Venation*.—Pattern: Pinnate. Color upper side: Near RHS Yellow-Green N144D. Color under side: Near RHS Green 138B.

*Petiole*.—Average Length: 5 to 11 mm. Diameter: 3 mm. Petiole color upper side: Near RHS Yellow-Green N144D. Petiole color under side: Near Green 138A. Petiole Texture upper side: Glabrous. Petiole Texture lower side: Glabrous.

FLOWER

Natural flowering season: Spring to early Summer.

Inflorescence type and habit: Terminal, pyramidal umbel.

Flower longevity on plant: 2 to 3 weeks.

Quantity of flowers per inflorescence: Approximately 140.

Inflorescence size:

*Width*.—Approximately 5 cm.

*Height*.—Approximately 8 cm.

Individual Flowers:

*Flower form*.—Rotate, single whorl.

*Flower aspect*.—Upward facing.

*Size*.—Diameter: Approximately 6 mm. Depth: Approximately 4 mm. Flower tube diameter: 1 mm. Flower tube length: 2 mm.

Flower other characteristics:
*Persistence*.—Self cleaning.
*Fragrance*.—Sweet.
Petal:
*Petal arrangement*.—Single whorl.
*Number of petals per flower*.—5.
*Petal shape*.—Orbicular to ovate.
*Petal base*.—Fused.
*Margin*.—Entire.
*Tip shape*.—Round.
*Length*.—2 mm.
*Width*.—1 to 2 mm.
*Texture*.—Upper: Smooth. Lower: Smooth. Tube: Smooth.
Petal color:
*When opening*.—Upper surface: Near RHS Yellow-White 158D. Lower surface: Near RHS Yellow-White 158D.
*Fully opened*.—Upper surface: Near RHS Yellow-White 158A. Lower surface: Near RHS Yellow-White 158B.
Bud:
*Shape*.—Oblong.
*Length*.—Approximately 3 mm.
*Diameter*.—Approximately 2 mm.
*Color*.—Near RHS Yellow-White 158D.
Sepals:
*Arrangement*.—Rotate, fused at base.
*Quantity*.—5.
*Shape*.—Individual sepals, narrow deltate.
*Base*.—Fused.
*Margin*.—Entire.
*Tip shape*.—Acute.
*Length*.—2 mm.
*Width*.—1 mm.
*Texture*.—Inner: Glabrous. Outer: Glabrous.
*Color*.—Inner: Green 143C. Outer: Green 137D.
Peduncle:
*Length*.—Average range 2.0 to 3.2 cm.
*Diameter*.—3 to 4 mm.
*Color*.—Near RHS Green 143C.
*Orientation*.—Straight, approximately 90° from branch.
*Strength*.—Good.
*Texture*.—Glabrous.
Pedicel:
*Length*.—3 mm.
*Diameter*.—1 mm.
*Color*.—Near RHS Green 143C.
*Strength*.—Good.
*Texture*.—Glabrous.

REPRODUCTIVE ORGANS

Stamens:
*Number*.—5.
*Filament length*.—1-2 mm.
*Filament color*.—Near RHS Yellow-White 158D.
Anthers:
*Shape*.—Linear.
*Length*.—1 mm.
*Color*.—Near RHS Greyed-Yellow 160A.
*Pollen*.—Scant, colored near Greyed-Yellow 160D.
Pistil:
*Number*.—1.
*Length*.—2 mm.
*Style*.—Length: 2 mm. Color: Near RHS Green 143C.
*Stigma*.—Color: Near RHS Green 143C.

OTHER CHARACTERISTICS

Seeds and fruits: Not observed to date.
Disease/pest resistance: Neither resistance nor susceptibility to normal diseases and pests of *Viburnum* have been observed.
Temperature tolerance: USDA Zones 8 to 11.

What is claimed is:

1. A new and distinct cultivar of *Viburnum* plant named 'COMPACT01' as herein illustrated and described.

* * * * *